United States Patent [19]

Ishikura et al.

[11] Patent Number: 4,898,996

[45] Date of Patent: Feb. 6, 1990

[54] PROCESS FOR PRODUCING 3-CHLORO-4-FLUORONITROBENZENE

[75] Inventors: Tsukasa Ishikura, Ageo; Tatuharu Fukushima, Yono, both of Japan

[73] Assignee: Nippon Kayaku Kabushiki Kaisha, Tokyo, Japan

[21] Appl. No.: 229,175

[22] PCT Filed: Mar. 18, 1988

[86] PCT No.: PCT/JP88/00283

§ 371 Date: Jun. 23, 1988

§ 102(e) Date: Jun. 23, 1988

[87] PCT Pub. No.: WO88/07519

PCT Pub. Date: Oct. 6, 1988

[30] Foreign Application Priority Data

Mar. 25, 1987 [JP] Japan .................................. 62-68792
Apr. 14, 1987 [JP] Japan .................................. 62-89751

[51] Int. Cl.$^4$ ........................ C07C 79/12; C07C 17/12
[52] U.S. Cl. ..................................... 568/938; 568/937; 568/939
[58] Field of Search ........................ 668/936, 937, 938

[56] References Cited

U.S. PATENT DOCUMENTS 4,446,075  5/1984  Erglmeier et al. ............. 568/938 X
4,456,777  6/1984  Petruck et al. ...................... 568/937

FOREIGN PATENT DOCUMENTS 56-131539 10/1981 Japan .
58-222040 12/1983 Japan ..................................... 79/12

OTHER PUBLICATIONS

Chemisches Zentralflatt 194 II p. 1432.
Receuil des Travaux Chimiques des Payo—Bas 51, (1932), pp. 98–113.
Japanese Abstract, vol. 8, No. 67, Mar. 29, 1984, Abstract No. C216, Abstract No. 58-222040, Inque, Fumio et al., "Preparation of M—Chlorobezotrifluoride".
Patent Abstracts of Japan, vol. 4, No. 54, Apr. 23, 1980, Abstract No. 55-24120, Kobayashi, "Preparation of 2,5—Dichlorobenzoic Acids".

Primary Examiner—Howard J. Locker
Assistant Examiner—Valerie D. Fee
Attorney, Agent, or Firm—Henry C. Nields

[57] ABSTRACT

A process for producing 3-chloro-4-fluoronitrobenzene which is characterized by chlorinating 4-fluoronitrobenzene in the presence of:
(1) iodine or an iodide in combination with iron or an iron compound or
(2) iodine or an iodide in combination with antimony or an antimony compound.

3 Claims, No Drawings

PROCESS FOR PRODUCING 3-CHLORO-4-FLUORONITROBENZENE

TECHNICAL FIELD

The present invention relates to a process for producing 3-chloro-4-fluoronitrobenzene. More specifically, the present invention relates to a process for producing 3-chloro-4-fluoronitrobenzene having a high purity with a high yield.

BACKGROUND ART

3-Chloro-4-fluoronitrobenzene is a useful compound as an intermediate for medicine and agricultural chemicals.

As industrial process for producing 3-chloro-4-fluoronitrobenzene, there has hitherto been known a process which comprises reacting 3,4-dichloronitrobenzene with excessive amount of potassium fluoride in a polar organic solvent at a high temperature. By this process, however, 3-chloro-4-fluoronitrobenzene cannot be obtained at a low cost due to the low yield and low purity, a large amount of expensive potassium fluoride used, requirement of a lot of cost for recovery of the polar organic solvent, etc.

The following reports disclose that 4-fluoronitrobenzene is subjected to chlorination to obtain 3-chloro-4-fluoronitrobenzene:

① Chemisches Zentralblatt. 1914 II page 1432,
② Recueil des Travaux Chimiques des Pays-Bas, 51 (1932) pages 98 to 101.

According to the processes described in the reports ① and ②, 4-fluoronitrobenzene is chlorinated in the presence of ferric chloride or iron powder. These processes, however, have a defect that a large amount of dichloro-4-fluoronitrobenzene are produced as by-products in addition of aimed 3-chloro-4-fluoronitrobenzene. And there is no description in which aimed compound was obtained in a high yield in the reports.

Thus, there is demanded a development of a process comprising chlorination of 4-fluoronitrobenzene, in which 3-chloro-4-fluoronitrobenzene is obtained with a high yield with lowering the production of dichloro-4-fluoronitrobenzene as by-products.

DISCLOSURE OF INVENTION

As the result of extensive researches for solving the problems as mentioned above, the present inventors have found that dichloro-4-fluoronitrobenzenes as the by-products are rarely formed by chlorinating 4-fluoronitrobenzene in the presence of specific substances and achieved the present invention thereon.

According to the present invention, there is provided a process for producing 3-chloro-4-fluoronitrobenzene which is characterized by chlorinating 4-fluoronitrobenzene in the presence of:

(1) iodine or an iodide in combination with iron or an iron compound, or
(2) iodine or an iodide in combination with antimony or an antimony compound.

BEST MODE FOR CARRYING OUT THE INVENTION

First, 4-fluoronitrobenzene used as a starting material in the process of the present invention is explained. 4-Fluoronitrobenzene is produced, for example, by directly nitrating fluorobenzene. Nitratoin of fluorobenzene is more advantageously carried out in sulfuric acid kept in a specific concentration at a temperature in a specific range.

The concentration (weight ratio) of sulfuric acid to be kept during the nitration reaction is selected in the range of 65 to 80%, preferably in the range of 70 to 78%.

The reaction temperature is 0° to 90° C., preferably 30° to 80° C., more preferably 40° to 70° C. As a nitrating agent, nitric acid is preferably used. The amount of nitric acid is preferably 1.0 to 1.1 times of the theoretical amount. As a method of addition of nitric acid, though nitric acid can be added alone, nitric acid is more preferably added in a state of mixed acids composed of nitric acid and sulfuric acid. The reaction time is usually 0.5 to 5 hours, though it varies depending on the reaction conditions. After completion of the reaction, the sulfuric acid layer is separated from oil layer and used by recycling. The oil layer is washed with warm water, then with an aqueous alkali solution followed by distillation to separate fluoromononitrobenzenes, respectively.

Thus obtained 4-fluoronitrobenzene is chlorinated in the presence of:

(1) iodine or an iodide in combination with iron or an iron compound, or
(2) iodine or an iodide in combination with antimony or an antimony compound.

The iodine and the iodides used in the process of the present invention include iodine, hydrogen iodide, iodine chloride, potassium iodide, sodium iodide, ferric iodide, antimony iodide and the like. Among them, particularly preferred are iodine, ferric iodide, iodine chloride and hydrogen iodide. The amount thereof to be used is usually 0.03 to 0.3% by weight, more preferably 0.01 to 1.0% by weight, based on the weight of 4-fluoronitrobenzene.

As the iron or the iron compounds, there may be used iron, ferric chloride, ferric hydroxide, ferric oxide, ferrous chloride, ferrous hydroxide, ferrous oxide and the like. Among them, preferred are ferrous chloride and ferric chloride. As the antimony or the antimony compounds, there may be used antimony, antimony pentachloride, antimony trichloride, antimony oxide, antimony hydroxide and the like. Among them, preferred are antimony pentachloride and antimony trichloride. The amount thereof to be used is usually 0.1 to 10% by weight, preferably 2 to 5% by weight, based on the weight of 4-fluoronitrobenzene.

The reaction temperature is usually in the range of 20° to 120° C., though it is not critical. The reaction time is usually 0.5 to 50 hours, though it varies depending on the reaction conditions. Though the reaction solvent is not always necessary, there may be used an organic solvent inert to chlorination such as perchlene, trichlene or the like.

As a chlorinating agent, chlorine gas is preferable, and the chlorine gas is preferably introduced until the starting material has been completely consumed with analyzing the amounts of the starting material and the product in the reaction solution.

The 3-chloro-4-fluoronitrobenzene obtained in the production process of the present invention has a purity enough to be used as it is industrially for an intermediate for medicines or for agricultural chemicals. However, if desired, it can be purified by crystallization, distillation or the like.

3-Chloro-4-fluoronitrobenzene is derived into 3-chloro-4-fluoroaniline by usual reduction reaction.

The process for producing 4-fluoronitrobenzene which is a starting material of the present invention is illustrated referring to Referencial Examples.

REFERENCIAL EXAMPLE

Process for producing 4-fluoronitrobenzene

Referencial Examples 1 and 2

Three reactors made of SUS were connected in cascade system. Fluorobenzene and a mixed acid ($HNO_3$—$H_2SO_4$—$H_2O$, weight ratios described in the following table) were poured into the first reactor at feeding rates of 94 ml/hr and 210 ml/hr, respectively, by quantitative feeding pumps at 50° to 55° C. (retention time: 1.5 hours).

After the reaction, oil layer was separated and washed with warm water, an aqueous alkali solution, then warm water to obtain fluoromononitrobenzenes.

TABLE

| | Composition of mixed acid | | | Conc. of $H_2SO_4$ during nitration | Yield | Composition | | |
|---|---|---|---|---|---|---|---|---|
| | $H_2SO_4$ | $HNO_3$ | $H_2O$ | | | Fluoro-benzene | Fluoromono-nitrobenzenes | Fluorodini-trobenzene |
| Ref. Ex. 1 | 61.7% | 20.3% | 18.0% | 72.5% | 98% | 0.5 | 99.5 | — |
| Ref. Ex. 2 | 63.6 | 20.3 | 16.1 | 75.0 | 98 | 0.4 | 99.6 | — |

The proportions of respective fluoromononitrobenzenes thus obtained in Referencial Examples 1 and 2 measured by gas chromatography were shown as follows:

| | p— | o— | m— |
|---|---|---|---|
| Referencial Example 1 | 85.0 | 14.7 | 0.3 |
| Referencial Example 2 | 85.1 | 14.6 | 0.3 |

Further, 1,000 g of the fluoromononitrobenzenes obtained in Referencial Example 1 were subjected to fractionating under reduced pressure to obtain 842 g of p-fluoronitrobenzene (purity: 99.8%) at 86.8° to 87.5° C./19 mm Hg and 137 g of o-fluoronitrobenzene (purity: 99.7%) at 100.7° to 101.2° C./19 mm Hg.

Referencial Example 3

A reactor made of SUS was charged with 48 g of fluorobenzene and 50 g of 72.5% sulfuric acid. Subsequently, a mixed acid ($H_2SO_4$:$HNO_3$:$H_2O$=62.3:19.6:18.1, weight ratio) was added dropwise at 50° to 55° C., over 40 minutes, then the mixture was stirred for 2 hours. The same succeeding procedures as in Referencial Example 1 were repeated to obtain 69.3 g (yield: 98%) of 4-nitromonofluorobenzenes. Analytical value by gas chromatography:
  Fluorobenzene: 0.5%
  Fluoromononitrobenzenes: 99.5%
  Fluorodinitrobenzene: -

The proportion of isomers in fluoromononitrobenzenes thus obtained was p-:o-:m-=85.2:14.5:0.3.

Referencial Example 4

The same procedures as in Referencial Example 3 were repeated, except that 50 g of 75.0% sulfuric acid and 135 g of a mixed acid ($H_2SO_4$:$HNO_3$:$H_2O$=61.0:25.4:13.6, weight ratio) were used, to obtain 69.1 g (yield: 98%) of fluoromononitrobenzenes. Analytical value by gas chromatography:
  Fluorobenzene: 0.3%
  Fluoromononitrobenzenes: 99.6%
  Fluorodinitrobenzene: 0.1%

The proportion of isomers in fluoromononitrobenzenes thus obtained was p-:o-:m-=85.0:14.7:0.3.

Referencial Example 5

A reactor made of SUS was charged with 48 g of fluorobenzene and 50 g of 72.5% sulfuric acid. Subsequently, 35.7 g of 96% nitric acid and 139.3 g of 78.3% sulfuric acid were simultaneously added dropwise at 50° to 55° C. over 1 hour. The same succeeding procedures as in Referencial Example 3 were repeated to obtain 68.8 g (yield: 98%) of fluoromononitrobenzenes. Analytical value by gas chromatography:
  Fluorobenzene: 0.4%
  Fluoromononitrobenzenes: 99.6%
  Fluorodinitrobenzene: -

The proportion of isomers in fluoromononitrobenzenes thus obtained was p-:o-:m-=85.3:14.4:0.3.

EXAMPLE

As mentioned above, according to the present invention, 3-chloro-4-fluoronitrobenzene is produced by using, as a starting material, the 4-fluoronitrobenzene obtained in these Referencial Examples preventing by-products from forming. The present invention is explained more specifically below.

Example 1

141 G of 4-fluoronitrobenzene, 3.8 g of ferric chloride and 0.2 g of iodine were charged and then heated. At a temperature of 60° to 70° C., chlorine gas was blown into the liquid until the starting material could not be detected (over 12 hours) to complete the reaction. Subsequently, the reaction mixture was washed three times with 100 g each of warm water followed by liquid separation to obtain 174 g (yield: 99%) of 3-chloro-4-fluoronitrobenzene. Analytical value thereof by gas chromatography was as follows:
  4-fluoronitrobenzene: 0.4%
  3-chloro-4-fluoronitrobenzene: 98.1%
  dichloro-4-fluoronitrobenzene: 1.4%

Example 2

141 G of 4-fluoronitrobenzene, 7 g of antimony pentachloride and 0.5 g of iodine were charged. The same succeeding procedures as in Example 1 were repeated to obtain 173 g (yield: 99%) of 3-chloro-4-fluoronitrobenzene. Analytical value thereof by gas chromatography was as follows:
  4-fluoronitrobenzene: 0.6%
  3-chloro-4-fluoronitrobenzene: 97.6%
  dichloro-4-fluoronitrobenzene: 1.6%

Examples 3 to 5

The almost same procedures as in Example 1 were repeated, except that the catalyst was replaced by each of those catalysts described in the item of catalyst of the following table to obtain the aimed 3-chloro-4-fluoronitrobenzene with a purity and a yield (as the analytical value by gas chromatography) shown in the table.

TABLE

| Example | Catalyst | | Yield (%) | Purity (%) |
| --- | --- | --- | --- | --- |
| 3 | Ferric chloride | 3.8 g | 98 | 97.7 |
|   | Iodine chloride | 0.5 g |    |      |
| 4 | Iron powder | 3.0 g | 99 | 97.6 |
|   | Iodine | 0.5 g |    |      |
| 5 | Antimony | 3.0 g | 98 | 97.3 |
|   | Iodine | 1.0 g |    |      |

Example 6

141 G of 4-fluoronitrobenzene, 11.5 g of ferric chloride and 0.6 g of iodine were charged and then heated. At a temperature of 50° to 55° C., 80 g of chlorine was blown into the liquid over 12 hours to complete the reaction. The same succeeding procedures as in Example 1 were repeated to obtain 174 g of 3-chloro-4-fluoronitrobenzene. Analytical value thereof by gas chromatography was as follows:

4-fluoronitrobenzene: 0.5%
3-chloro-4-fluoronitrobenzene: 97.9%
dichloro-4-fluoronitrobenzene: 1.3%

Comparative Example 1

Chlorine gas was blown in the same manner as in Example 1, except that the iodine was not used.

The proportion of the starting material and the product in the reaction solution was as follows:

4-fluoronitrobenzene: 98.3%
3-chloro-4-fluoronitrobenzene: trace

Comparative Example 2

The reaction was carried out in the same manner as in Example 1, except that the iodine was not used and the reaction temperature was 125° to 135° C.

The proportion of the starting material and products in the reaction solution was as follows:

4-fluoronitrobenzene: 2.0%
3-chloro-4-fluoronitrobenzene: 91.5%
dichloro-4-fluoronitrobenzene: 5.7%

Industrial Applicability

As 4-fluoronitrobenzene is chlorinated in the presence of specific compound (catalysts) to obtain a high pure 3-chloro-4-fluoronitrobenzene useful as an intermediate for medicines and agricultural chemicals with a high yield, so the process of the present invention can be mentioned as a process having an extremely high industrial applicability.

We claim:

1. A process for producing 3-chloro-4-fluoronitrobenzene comprising chlorinating 4-fluoronitrobenzene in the presence of:
   (1) iodine or an iodide in combination with iron or an iron compound or
   (2) iodine or an iodide in combination with antimony or an antimony compound.

2. A production process according to claim 1, wherein the chlorination is carried out in the presence of iodine in combination with ferrous chloride or ferric chloride.

3. A production process according to claim 1, wherein the chlorination is carried out in the presence of iodine in combination with antimony trichloride or antimony pentachloride.

* * * * *